US008864853B2

(12) United States Patent
Beilfuss et al.

(10) Patent No.: US 8,864,853 B2
(45) Date of Patent: Oct. 21, 2014

(54) ADDITIVE MIXTURE FOR THE BACTERICIDAL AND ANTICORROSIVE ADDITIZATION OF FUELS

(75) Inventors: Wolfgang Beilfuss, Hamburg (DE); Ralf Gradtke, Tornesch (DE); Jennifer Knopf, Hamburg (DE); Ingo Krull, Kummerfeld (DE)

(73) Assignee: l'Air Liquide Societe Anonyme pour l'etude et L'exploitation des Procedes Georges Claude, Paris (FR)

( * ) Notice: Subject to any disclaimer, the term of this patent is extended or adjusted under 35 U.S.C. 154(b) by 47 days.

(21) Appl. No.: 13/383,901

(22) PCT Filed: Jun. 21, 2010

(86) PCT No.: PCT/EP2010/058701
§ 371 (c)(1),
(2), (4) Date: Jan. 13, 2012

(87) PCT Pub. No.: WO2011/006734
PCT Pub. Date: Jan. 20, 2011

(65) Prior Publication Data
US 2012/0110899 A1 May 10, 2012

(30) Foreign Application Priority Data

Jul. 13, 2009 (DE) .......... 10 2009 033 161

(51) Int. Cl.
| | | |
|---|---|---|
| C10L 1/233 | (2006.01) |
| A01N 43/66 | (2006.01) |
| A01N 43/76 | (2006.01) |
| A61K 31/53 | (2006.01) |
| A61K 31/42 | (2006.01) |
| A01N 35/00 | (2006.01) |
| C10M 141/06 | (2006.01) |
| C10L 1/14 | (2006.01) |
| C10L 1/22 | (2006.01) |
| C10L 1/19 | (2006.01) |
| C10L 1/223 | (2006.01) |
| C10L 1/183 | (2006.01) |
| C10L 1/16 | (2006.01) |
| C10L 1/185 | (2006.01) |
| C10L 1/222 | (2006.01) |
| C10L 1/232 | (2006.01) |

(52) U.S. Cl.
CPC ............ *C10L 1/14* (2013.01); *C10M 2207/046* (2013.01); *A01N 35/00* (2013.01); *C10M 2215/225* (2013.01); *C10M 141/06* (2013.01); *C10N 2230/16* (2013.01); *C10L 1/19* (2013.01); *C10N 2270/02* (2013.01); *C10L 1/223* (2013.01); *C10L 1/1832* (2013.01); *C10L 1/1616* (2013.01); *C10L 1/1608* (2013.01); *C10M 2207/289* (2013.01); *C10L 1/1855* (2013.01); *C10N 2230/12* (2013.01); *C10L 1/233* (2013.01); *C10L 1/2227* (2013.01); *C10M 2215/221* (2013.01); *C10M 2207/026* (2013.01); *C10M 2215/102* (2013.01); *C10L 1/22* (2013.01); *C10M 2203/104* (2013.01); *C10L 1/232* (2013.01); *C10M 2215/223* (2013.01); *C10M 2215/22* (2013.01); *C10M 2215/223* (2013.01); *C10M 2215/224* (2013.01)
USPC ............... 44/433; 44/344; 514/241; 514/242; 514/243

(58) Field of Classification Search
USPC .............. 514/241–243; 123/1 A; 44/334, 433
See application file for complete search history.

(56) References Cited

U.S. PATENT DOCUMENTS

| | | | |
|---|---|---|---|
| 7,781,467 B2 * | 8/2010 | Gradtke et al. ............... | 514/374 |
| 7,935,701 B2 * | 5/2011 | Gradtke et al. ............... | 514/241 |
| 8,084,880 B2 * | 12/2011 | Botan et al. ..................... | 290/55 |
| 8,349,881 B2 * | 1/2013 | Gradtke et al. ............... | 514/374 |
| 2001/0021711 A1 * | 9/2001 | Beilfuss et al. ............... | 514/245 |
| 2005/0054642 A1 * | 3/2005 | Gradtke et al. ............... | 514/241 |
| 2005/0210739 A1 * | 9/2005 | Esen et al. ..................... | 44/605 |
| 2006/0223806 A1 * | 10/2006 | Gradtke et al. ............... | 514/241 |
| 2009/0013591 A1 * | 1/2009 | Bradin et al. .................. | 44/452 |
| 2009/0099188 A1 * | 4/2009 | Gradtke et al. ............... | 514/241 |
| 2010/0216677 A1 * | 8/2010 | Gradtke et al. ............... | 508/307 |

FOREIGN PATENT DOCUMENTS

| | | |
|---|---|---|
| EP | 0 330 416 A1 | 8/1989 |
| EP | 1 402 778 A1 | 3/2003 |
| EP | 1 800 539 A1 | 6/2007 |
| EP | 1800539 A1 * | 6/2007 |
| GB | 1 505 069 A | 3/1978 |

OTHER PUBLICATIONS

Sarin A et al: "Influence of metal contaminants on oxidation stability of Jatropha biodiesel", ENERGY, vol. 34, No. 9, Sep. 1, 2009, pp. 1271-1275, Pergamon Press, Oxford, GB, XP026459700.
Dinkov R et al: "Effect of commercially available antioxidants over biodiesel/diesel blends stability", FUEL, IPC Science and Technology Press, vol. 88, No. 4, Apr. 1, 2009, pp. 732-737, Guildford, GB, XP025873015.
International Search Report, dated Nov. 2, 2011, in PCT/EP2010/058701.

* cited by examiner

*Primary Examiner* — Pamela H Weiss
(74) *Attorney, Agent, or Firm* — Young & Thompson

(57) ABSTRACT

An additive mixture for fuels including a) at least one N-formal, b) at least one antioxidant and c) at least one corrosion inhibitor. The additive mixture ensures that the additized fuels and lubricants have biocidal and corrosion-inhibiting additization, especially when they include proportions of renewable raw materials, such as biodiesel, and when they are in contact with copper-containing surfaces.

13 Claims, No Drawings

ADDITIVE MIXTURE FOR THE BACTERICIDAL AND ANTICORROSIVE ADDITIZATION OF FUELS

The invention relates to an additive mixture for the bactericidal and anticorrosive additization of fuels. The additive can be formulated as a liquid concentrate or as a semiconcentrate. The invention further relates to the use of the additive mixture for bactericidal and anticorrosive additization of fuels, and to correspondingly additized fuels. The invention also relates to a method for operating a system with a fuel which comprises the components of the inventive additive mixture.

In systems which come into contact with fuels (such as heating oil) (storage tanks, conduits, valves, filters, probes, measuring instruments, burners, etc.), different materials are used, for example plastics, metals and alloys, especially copper-containing materials. Owing to the interaction of long storage times, different compositions of the fuel and external influences such as formation of water of condensation, and oxidative and/or microbial degradation processes, the composition of the fuel can change and lead to undesired consequent phenomena. These consequent phenomena include corrosion, turbidity up to and including precipitation (formation of "sludge"), blockage of filters and material wear. This can lead to failure of the system and to the necessity of expensive repairs. Similar problems arise in fuel-processing systems such as stationary and mobile diesel engines and the corresponding injection systems.

The prior art discloses biocidal compositions for fuels. For example, DE 103 40 830 A1 describes compositions based on formaldehyde depot compounds and antioxidants, and the use thereof for preserving industrial products, for example fuels. An illustrative formaldehyde depot compound is N,N'-methylenebis(5-methyloxazolidine), which is sold by Schülke & Mayr GmbH (Norderstedt, Federal Republic of Germany) as Grotan® OX (Grotamar® 71, Mar° 71). The compositions have very good storability as concentrates and have a constantly low level of deformation of the plastic vessel containing the concentrate ("neck-in effect").

DE 199 61 621 A1 relates to compositions which comprise a bactericidal N-formal, a fungicide and a stabilizer, for use, for example, in fuel additives. The compositions are storage-stable and have good meterability.

In the systems mentioned, as well as fossil fuels such as mineral oil, biofuels (such as biodiesel) are increasingly being used, which comprise fatty acid alkyl esters such as fatty acid methyl esters (FAME), for example rapeseed oil methyl ester (RME). This is both because of legal stipulations and financial support and because of the insight that, in the generation of energy from renewable raw materials, the release of $CO_2$ is climate-neutral. Since the use of biofuels, however, there has been a significant increase in material compatibility problems. It is assumed that biodiesel, for example, leaches copper ions out of copper-containing constituents of the systems. The increased copper ion content in turn accelerates the decomposition of the biodiesel and ultimately leads to the problems mentioned above.

WO2009/060057 A2 relates to the use of water-soluble biocides in biodiesel. An example of a biocide is 3,3'-methylenebis(5-methyloxazolidine). To improve the efficacy of the biocides, ethers are proposed. The ethers according to WO2009/060057 A2 are needed in a certain amount to dissolve the biocides in the biodiesel. However, ethers readily form peroxides which can convert constituents in biodiesel, inactivate antioxidants and wear away material. The biocidal activity of ethers, moreover, is not comparable to that of formaldehyde depot compounds, and therefore (also as boosters) have to be used at a higher concentration and are therefore uneconomic. Moreover, ethers have a comparatively low flashpoint and can lead to less favorable labelling of products.

For this reason, it is desirable to add to the fuel improved additives which suppress these troublesome influences (decomposition of the biodiesel, formation of sludge) or do not allow them to arise at all, without necessarily needing to use ethers. More particularly, it was an object of the present invention to provide additive mixtures which are suitable for biocidal and anticorrosive additization of those fuels which comprise proportions of renewable raw materials, for example biodiesel. The additive mixtures should also be stable as concentrates and be easy to dose.

It has now been found that, surprisingly, these objects are achieved by an additive mixture which comprises
a) at least one N-formal,
b) at least one antioxidant and
c) at least one corrosion inhibitor.

Inventive additives protect fuels to which they are added from infestation by bacteria, yeasts and moulds, and at the same time provide them with the necessary corrosion protection. The advantages of the additive mixtures are found more particularly in the case of addition to fuels which comprise components composed of renewable raw materials, for example biodiesel.

a) N-Formal

Inventive additive mixtures comprise at least one N-formal. The advantages of these active microbicidal ingredients are disclosed in DE 103 40 830 A1. Particularly suitable N-formals are reaction products of formaldehyde and amines (preferably alkanolamines) with a molar formaldehyde excess.

Examples of N-formals are condensation products of paraformaldehyde and isopropanolamine in a molar ratio of 3:2, condensation products of paraformaldehyde and isopropanolamine in a molar ratio of 3:2 and urea, and condensation products of paraformaldehyde and isopropanolamine in a molar ratio of 3:2 and urea and ethylene glycol.

N-Formals which are used with preference in accordance with the invention are N,N'-methylenebis(5-methyloxazolidine), $\alpha,\alpha',\alpha''$-trimethyl-1,3,5-triazine-1,3,5-(2H,4H,6H)triethanol, 4,4-dimethyloxazolidine, dimethylolurea, 5-ethyl-3,7-dioxa-1-azabicyclo[3.3.0]octane, 2-(hydroxymethylamino)ethanol, methylenebistetrahydro-1,3-bisoxazine, 5-methylolchloro-acetamide, bis(hydroxymethyl)-5,5-dimethylhydantoin, diazolidinylurea, sodium hydroxymethylglycinate and 3,4,4-trimethyloxazolidine, 2,2',2''-(hexahydro-1,3,5-triazine-1,3,5-triyl)triethanol (Grotan® BK), tetrahydro-1,3,4,6-tetrakis(hydroxylmethyl)imidazo[4,5-d]imidazole-2,5-(1H,3H)dione (TMAD) and tetramethylolglycoluril.

Preference is given to low-water formaldehyde depot compounds.

Particular preferred formaldehyde depot compounds are 3,3'-methylenebis(5-methyloxazolidine), 2,2',2''-(hexahydro-1,3,5-triazine-1,3,5-triyl)-triethanol, $\alpha,\alpha',\alpha''$-trimethyl-1,3,5-triazine-(2H,4H,6H)triethano 1, tetrahydro-1,3,4,6-tetrakis(hydroxymethyl)imidazo[4,5-d]imidazole-2,5(1H,3H)-dione, dimethylurea and the products Grotan OF (methylenebis(5-methyloxazolidine)+urea) and Grotan OK (methylenebis(5-methyloxazolidine)+urea+ethylene glycol).

A very particularly preferred formaldehyde depot compound is 3,3'-methylenebis(5-methyloxazolidine).

b) Antioxidant

The inventive additive mixture comprises at least one antioxidant. Preferred antioxidants are liquid or are sufficiently soluble in the formaldehyde depot compound at room temperature. Examples of antioxidants are selected from sterically hindered phenols, amines, vitamin E and derivatives thereof, and alkyl gallates, preferably 3-tert-butyl-4-hydroxyanisole (BHA), 2,6-di-tert-butyl-p-cresol (BHT), 2,6-di-tert-butylphenol, lauryl gallate and vitamin E.

Especially preferred as antioxidants are 2,6-di-tert-butylphenol and BHT.

c) Corrosion Inhibitor

The inventive additive mixture comprises, as a further obligatory component c), at least one corrosion inhibitor. Preferred corrosion inhibitors are liquid or are sufficiently soluble in the formaldehyde depot compound at room temperature. Particularly preferred corrosion inhibitors are triazole derivatives, for example benzotriazole, tolyltriazole or N,N-bis(2-ethylhexyl)((1,2,4-triazol-1-yl)methyl)amine.

Particular preference is given to using N,N-bis(2-ethylhexyl)((1,2,4-triazol-1-yl)methyl)amine, which is supplied by BASF SE (Ludwigshafen, Federal Republic of Germany) as Irgamet® 30.

Amounts of Components a), b) and c)

In additive mixtures preferred in accordance with the invention, the weight ratio of component b) to component c) is typically 20:1 to 1:20, preferably 1:10 to 10:1, especially 1:4 to 4:1, for example 1:1.

As explained hereinafter, inventive additives are typically formulated as liquid concentrates or semiconcentrates.

Liquid Concentrate

In inventive additive mixtures formulated as liquid concentrates, the proportion of component a) is preferably at least 60% by weight, preferably at least 80% by weight, especially at least 90% by weight, for instance 92% by weight. The proportions of components b) and c) are typically each at least 0.5% by weight, preferably at least 1% by weight, especially at least 2 by weight, for instance 4% by weight. Particular preference is given to liquid concentrates which consist of components a), b) and c), i.e. comprise no further constituents.

A particularly preferred liquid concentrate consists of:
a) 92% by weight of 3,3'-methylenebis(5-methyloxazolidine),
b) 4% by weight of 2,6-di-tert-butylphenol and
c) 4% by weight of Irgamet 30.

The liquid concentrate is prepared by initially charging component a) (for example 3,3'-methylenebis(5-methyloxazolidine)) and then dissolving component b) (such as 2,6-di-tert-butylphenol or BHT) and component c) (such as Irgamet 30) while stirring. The product is clear and colourless to pale yellow.

Inventive liquid concentrates are used prophylactically in fuels which are yet to be microbially infested in concentrations of 20 to 100 mg/l (ppm), and in fuels which have already been contaminated in amounts of 200 to 1000 ppm.

Semiconcentrate

In inventive additive mixtures which have been formulated as a semiconcentrate, the proportion of component a) is typically at least 5% by weight, preferably at least, preferably at least 10% by weight, especially at least 15% by weight, for instance 20% by weight. Components b) and c) are typically present in an amount of in each case at least 0.1% by weight, preferably at least 0.25% by weight, especially at least 0.5% by weight, for instance 0.9% by weight.

Semiconcentrates comprise, as well as the inventive components a), b) and c), a carrier. Examples of carriers are selected from diesel oil, biodiesel oil, fatty acid methyl esters, mineral oil (e.g. Shellsol A 150), aliphatic or aromatic hydrocarbons (such as toluene), alkylbenzenes, for example Marlican (RG), and mixtures thereof. The amount of the carrier in the concentrate is preferably at least 50% by weight, more preferably at least 60% by weight, especially at least 70% by weight, for instance 78% by weight.

A particularly preferred semiconcentrate comprises:
a) 20% by weight of 3,3'-methylenebis(5-methyloxazolidine),
b) 0.9% by weight of 2,6-di-tert-butylphenol
c) 0.9% by weight of Irgamet 30 and, as the remainder, a hydrocarbon as a carrier which is soluble in FAME-containing hydrocarbons, for example diesel fuel. For example, the carriers used are, for example, ShellSol A 150 or alkylbenzene (Marlican).

To prepare the semiconcentrate, the carrier is initially charged and component a) (such as 3,3'-methylenebis(5-methyloxazolidine)), component b) (such as 2,6-di-tert-butylphenol or BHT) and component c) (such as Irgamet 30) are dissolved while stirring. The product is clear and colourless to pale yellow.

Inventive semiconcentrates are used prophylactically in fuels which are yet to be microbially infested in concentrations of 100 to 500 ppm, and in fuels which have already been contaminated in amounts of 1000 to 5000 ppm.

The invention further relates to the use of the inventive additive mixture for biocidal and anticorrosive additization of fuels, and to the protection thereof from oxidative degradation.

According to the invention, the corrosion of copper in particular as a constituent of the materials of systems through which the fuel flows or in which it is stored. As mentioned above, the corrosion of copper presented a problem especially when the fuel comprises proportions of renewable raw materials, for example FAME. The proportion of renewable raw materials (such as FAME) which is typically present in the fuel is up to 100% by volume, preferably up to 20% by volume, especially up to 10% by volume, such as 5 to 7% by volume.

According to the invention, components a), b) and c) are used in the fuel in an amount which ensures effective protection from microbial attack and from oxidative and corrosive influences. In the fuel, the proportion of component a) should be at least 5 ppm, more preferably at least 100 ppm and especially preferably at least 200 ppm, for example 500 ppm. The proportions of components b) and c) should each be at least 0.25 ppm, preferably at least 5 pmm and more preferably at least 10 ppm, for example 25 ppm.

The invention further relates to the use of the inventive liquid concentrate for producing a semiconcentrate.

Components a), b) and c) are used—in combination—in fuels, preferably in the form of the inventive liquid concentrates or semiconcentrates. They are used in accordance with the invention in lubricants, cooling lubricant concentrates and emulsions, transformer oils, fuels, biofuels, biodiesels, diesel fuels, kerosenes, heavy oils, heating oils, mineral oils, all of which are referred to here as fuels. They are preferably used in fuels with proportion of material composed of renewable raw materials, especially biodiesel.

The inventive formulations can be combined with further active biocidal ingredients, functional additives and auxiliaries, as disclosed, for example, in WO2009/060057 A2, DE 10 2006 035013 A1 or DE 103 40 830 A1.

The combination of components a), b) and c) is used in fuels preferably by adding a liquid concentrate or a semiconcentrate. Alternatively, it is possible to add components a), b) and c) individually, but this alternative is not preferred.

The invention further relates to a method for operating a system with a fuel, in which the additive mixture described is added to the fuel, or in which the components are added individually.

The invention also relates to a fuel which comprises components a), b) and c) in such an amount that the concentration (based in each case on the fuel)

- of component a) is at least 5 ppm, preferably at least 100 ppm and especially at least 200 ppm, for instance 500 ppm;
- of component b) is at least 0.25 ppm, preferably at least 5 ppm and especially at least 10 ppm, for instance 25 ppm; and
- of component c) is at least 0.25 ppm, preferably at least 5 pmm and especially at least 10 ppm, for instance 25 ppm.

The inventive liquid concentrates or semiconcentrates have the following advantages:

- they are clear, homogeneous, fluid, low-viscosity, free-flowing, low-odour, readily distributable, readily incorporable, possess good stability (cold stability, storage stability, sufficient thermal stability) and are easy to handle;
- they have a broad profile of action: they are bactericidally, fungicidally and algicidally active, protect from oxidative degradation, give a good coating on the surfaces to be treated, protect from corrosion, especially in the case of nonferrous metals;
- they protect systems and materials which come into contact with fuels, especially biofuels;
- they effectively prevent sludge formation in fuel systems and vessels;
- they improve the shelf life of the treated products;
- they improve the lubricant properties of the treated products;
- they possess good compatibility with a multitude of materials;
- they have good solubility in different bases, such as oils;
- they possess good dissolution capacity for further/additional additives;
- no additional solvents are required and
- they enhance the calorific value of heating oil.

The advantages of the invention are evident more particularly from the examples which follow.

EXAMPLES

Unless stated otherwise, all percentages are based on weight.

Example 1

Materials used:
3,3'-methylenebis(5-methyloxazolidine)
brass 63 (100×20×1 mm), Cat. No.: 16-24 from Riegger Industriehandel, Reinbek, Federal Republic of Germany
E-copper ((100×20×1 mm), Cat. No.: 15-54 from Riegger
diesel fuel to EN 590, with 5% (V/V) fatty acid methyl ester Procedure: The solutions and the metal sheet were each introduced into a 500 ml wide-neck bottle. Solutions 1A-1C were not stirred; solutions 1D-1G were stirred with a magnetic stirrer. The appearance of the solutions was assessed visually.

| Sample | Experiment | Start | After 4 weeks | After 6 weeks |
|---|---|---|---|---|
| 1A | Cu sheet in diesel; without stirring | clear yellow solution | clear yellow solution | clear yellow solution |
| 1B | Cu sheet in diesel + 500 ppm of 3,3'-methylenebis(5-methyl-oxazolidine); without stirring | clear yellow solution | clear yellow solution | slightly turbid yellow solution |
| 1C | Cu sheet in diesel + 50 ppm of 3,3'-methylenebis(5-methyl-oxazolidine); without stirring | clear yellow solution | clear yellow solution | turbid yellow solution |
| 1D | Cu sheet in diesel; with stirring | clear yellow solution | clear yellow solution | clear yellow solution |
| 1E | Cu sheet in diesel + 500 ppm of 3,3'-methylenebis(5-methyl-oxazolidine); with stirring | clear yellow solution | clear yellow solution | highly turbid solution, some dark coating on the sheet and at the base of the bottle |
| 1F | Cu sheet in diesel + 50 ppm of 3,3'-methylenebis(5-methyl-oxazolidine); with stirring | clear yellow solution | clear yellow solution | clear yellow solution, fluff in the solution |
| 1G | Brass sheet in diesel + 500 ppm of 3,3'-methylenebis(5-methyl-oxazolidine); with stirring | clear yellow solution | clear yellow solution | turbid yellow solution, some dark coating on the sheet and at the base of the bottle |

Example 2

Materials used:
3,3'-methylenebis(5-methyloxazolidine)
semiconcentrate 2: 20% 3,3'-methylenebis(5-methyloxazolidine), 0.9% di-tert-butylphenol, 0.9% Irgamet 30; dissolved in ShellSol A 150
E-copper (100×20×1 mm), Cat. No.: 15-54 from Riegger
diesel fuel to EN 590, with 5% (V/V) fatty acid methyl ester content Procedure: The solutions and the metal sheet were each introduced into a 500 ml wide-neck bottle and stirred at room temperature with a magnetic stirrer.

| Sample | |
|---|---|
| 2A | Diesel, stirred |
| 2B | Diesel + copper sheet, stirred |
| 2C | Diesel + 500 ppm of 3,3'-methylenebis (5-methyloxazolidine); stirred |
| 2D | Diesel + copper sheet + 500 ppm 3,3'-methylenebis (5-methyloxazolidine) |
| 2E | Diesel + 2500 ppm of semiconcentrate 2, stirred |
| 2F | Diesel + copper sheet + 2500 ppm of semiconcentrate 2, stirred |

| Copper content mg/l (ppm) | 2 days | 1 week | 2 weeks | 3 weeks | 6 weeks |
|---|---|---|---|---|---|
| 2A | 0.1 | 0.1 | 0.2 | not determined | 0.1 |
| 2B | 1.3 | 1.5 | 1.8 | 1.6 | 2.3 |
| 2C | 0.1 | 0.1 | 0.1 | 0.1 | 0.2 |
| 2D | 0.6 | 0.6 | 0.8 | 1.0 | 1.0 |
| 2E | 0.1 | <0.1 | <0.1 | <0.1 | 0.2 |
| 2F | not determined | 0.5 | not determined | 0.7 | 0.7 |

| Appearance | 2A | 2B | 2C | 2D | 2E | 2F |
|---|---|---|---|---|---|---|
| Start | clear yellow solution | clear yellow solution | clear yellow solution | clear yellow solution | clear yellow solution | clear yellow solution |
| after 1 week | clear yellow solution | clear yellow solution | clear yellow solution | clear yellow solution | clear yellow solution | clear yellow solution |
| after 2 weeks | clear yellow solution | clear yellow solution | clear yellow solution | clear yellow solution | clear yellow solution | clear yellow solution |
| after 3 weeks | clear yellow solution | clear yellow solution | clear yellow solution | clear yellow solution | clear yellow solution | clear yellow solution |
| after 5 weeks | clear yellow solution | clear yellow solution | clear yellow liquid | turbid yellow solution | clear yellow solution | clear yellow solution |
| after 10 weeks | clear yellow solution | turbid yellow liquid | clear yellow solution | red sludge at the base of a turbid yellow liquid | clear yellow solution | clear yellow solution |
| after 11 weeks | clear yellow solution | red sludge at the base of a turbid yellow liquid | clear yellow solution | red sludge at the base of a turbid yellow liquid | clear yellow solution | clear yellow solution |
| after 12 weeks | clear yellow solution | red sludge at the base of a turbid yellow liquid | clear yellow solution | red sludge at the bottom of a turbid yellow liquid | clear yellow solution | clear yellow solution |
| after 13 weeks | clear yellow solution | red sludge at the base of a turbid yellow liquid | turbid | red sludge at the base of a turbid yellow liquid | somewhat more intense yellow | somewhat more intense yellow |
| after 14 weeks | clear yellow solution | red sludge at the base of a turbid yellow liquid | turbid, a little brown sludge at the base | red sludge at the base of a turbid yellow liquid | somewhat more intense yellow | somewhat more intense yellow, brown crumbs in the solution |
| after 15 weeks | clear yellow solution | red sludge at the base of a turbid yellow liquid | turbid, a little brown sludge at the base | red sludge at the base of a turbid yellow liquid | somewhat more intense yellow | somewhat more intense yellow, brown crumbs in the solution |
| after 20 weeks | clear yellow solution | red sludge at the base of a turbid yellow liquid | turbid, a little brown sludge at the base | red sludge at the base of a turbid yellow liquid | slightly turbid, somewhat more intense yellow | slightly turbid, somewhat more intense yellow, brown crumbs/fluff in the solution |

Example 3

Materials used:
Concentrate X: 92% 3,3'-methylenebis(5-methyloxazolidine)+4% BHT+4% benzotriazole
Concentrate Y: 92% 3,3'-methylenebis(5-methyloxazolidine)+4% 2,6-di-tert-butylphenol+4% Irgamet 30
E-copper (100×20×1 mm), Cat. No.: 15-54 from Riegger diesel fuel to EN 590, with 5% (V/V) fatty acid methyl ester content Procedure: The solutions and the metal sheet were each introduced into a 500 ml bottle and stirred with a magnetic stirrer.

| Sample | |
|---|---|
| 3A | Diesel + 500 ppm of concentrate X, stirred |
| 3B | Diesel + 500 ppm of concentrate X + copper sheet, stirred |
| 3C | Diesel + 500 ppm of concentrate Y, stirred |
| 3D | Diesel + copper sheet + 500 ppm of concentrate Y; stirred |

| Copper content mg/l (ppm) | Blank value | 3 weeks | 6 weeks |
|---|---|---|---|
| 3A | 0.2 | 0.2 | 0.16 |
| 3B | 0.2 | 1.4 | 2.1 |
| 3C | 0.2 | 0.2 | 0.25 |
| 3D | 0.2 | 0.7 | 0.67 |

| Appearance | 3A | 3B | 3C | 3D |
|---|---|---|---|---|
| Start | clear yellow solution | clear yellow solution | clear yellow solution | clear yellow solution |
| after 3 weeks | clear yellow solution | clear yellow solution | clear yellow solution | clear yellow solution |
| after 6 weeks | clear yellow solution | clear yellow solution | clear yellow solution | clear yellow solution |
| after 7 weeks | clear yellow solution | clear yellow solution | clear yellow solution | clear yellow solution |
| after 8 weeks | clear yellow solution | clear yellow solution | clear yellow solution | clear yellow solution |
| after 9 weeks | clear yellow solution | clear yellow solution | clear yellow solution | clear yellow solution |
| after 10 weeks | clear yellow solution | slightly turbid, brown fluff | clear yellow solution | clear yellow solution |
| after 11 weeks | clear yellow solution | turbid, brown sludge at the base | clear yellow solution | clear, intensely yellow solution |
| after 12 weeks | clear yellow solution | turbid, brown sludge at the base | clear yellow solution | clear, intensely yellow solution |
| after 17 weeks | slightly turbid, yellow | turbid, brown sludge at the base | very slightly turbid, yellow | turbid, fluff/crumbs in the solution |

Example 4

Materials used:

3,3'-Methylenebis(5-methyloxazolidine)

Semiconcentrate 4: 20% 3,3'-methylenebis(5-methyloxazolidine), 0.9% di-tert-butylphenol, 0.9% Irgamet 30; dissolved in ShellSol A 150

Diesel fuel to EN 590, with 5% (V/V) fatty acid methyl ester content

Copper naphthenate (copper content: 7.97%; stock solution: 12.55 g of copper naphthenate are dissolved/100 g of toluene, corresponding to 1% copper)

| Sample | Test setup |
|---|---|
| 4A | Diesel |
| 4B | Diesel + 500 ppm of 3,3'-methylenebis(5-methyloxazolidine) |
| 4C | Diesel + 2500 ppm of semiconcentrate 4 |
| 4D | Diesel + 1 ppm of copper + 500 ppm of 3,3'-methylenebis(5-methyloxazolidine) |
| 4E | Diesel + 5 ppm of copper + 500 ppm of 3,3'-methylenebis(5-methyloxazolidine) |
| 4F | Diesel + 1 ppm of copper + 2500 ppm of semiconcentrate 4 |
| 4G | Diesel + 5 ppm of copper + 2500 ppm of semiconcentrate 4 |
| 4H | Diesel + 1 ppm of copper (after 2 weeks) |
| 4I | Diesel + 5 ppm of copper (after 2 weeks) |

All samples are stirred in a 250 ml screwtop bottle with a magnetic stirrer at room temperature. The appearance changed as follows:

| Appearance | 4A | 4B | 4C | 4D | 4E | 4F | 4G | 4H | 4I |
|---|---|---|---|---|---|---|---|---|---|
| Start | clear yellow solution | clear yellow solution | clear yellow solution | clear yellow solution | clear yellow solution | clear yellow solution | clear yellow solution | | |
| after 2 weeks | clear yellow solution | clear yellow solution | clear yellow solution | turbid yellow liquid | turbid yellow liquid | clear yellow solution | clear yellow solution | clear yellow solution | clear yellow solution |

-continued

| Appearance | 4A | 4B | 4C | 4D | 4E | 4F | 4G | 4H | 4I |
|---|---|---|---|---|---|---|---|---|---|
| after 3 weeks | clear yellow solution | clear yellow solution | clear yellow solution | turbid yellow liquid | dark sludge in turbid yellow liquid | clear yellow solution | clear yellow solution | clear yellow solution | turbid yellow liquid |
| after 4 weeks | clear yellow solution | clear yellow solution | clear yellow solution | dark sludge in turbid yellow liquid | dark sludge in turbid yellow liquid | clear yellow solution | clear yellow solution | dark sludge in turbid yellow liquid | dark sludge in turbid yellow liquid |
| after 5 weeks | clear yellow solution | clear yellow solution | clear yellow solution | dark sludge in turbid yellow liquid | dark sludge in turbid yellow liquid | clear yellow solution | turbid, flocs | dark sludge in turbid yellow liquid | dark sludge in turbid yellow liquid |
| after 6 weeks | clear yellow solution | clear yellow solution | clear yellow solution | dark sludge in turbid yellow liquid | dark sludge in turbid yellow liquid | clear yellow solution | turbid, flocs | dark sludge in turbid yellow liquid | dark sludge in turbid yellow liquid |
| after 7 weeks | clear yellow solution | clear yellow solution | clear yellow solution | dark sludge in turbid yellow liquid | dark sludge in turbid yellow liquid | turbid, yellow, flocs | turbid, flocs | dark sludge in turbid yellow liquid | dark sludge in turbid yellow liquid |
| after 12 weeks | clear yellow solution | clear yellow solution | clear yellow solution | dark sludge in turbid yellow liquid | dark sludge in turbid yellow liquid | turbid, yellow, flocs | turbid, flocs | dark sludge in turbid yellow liquid | dark sludge in turbid yellow liquid |

Example 5

Materials used:

EL heating oil, low-sulfur (purely mineral, no fatty acid methyl esters)

Fatty acid methyl esters 3,3'-Methylenebis(5-methyloxazolidine)

Semiconcentrate X: 20% 3,3-methylenebis(5-methyloxazolidine), 0.9% di-tert-butylphenol, 0.9% Irgamet 30; dissolved in ShellSol A 150

E-copper (100×20×1 mm) Cat. No.: 15-4 from Riegger

| Diesel sample | Composition (% by vol.) |
|---|---|
| 5A | 100% heating oil + 0% biodiesel |
| 5B | 90% heating oil + 10% biodiesel |
| 5C | 80% heating oil + 20% biodiesel |
| 5D | 70% heating oil + 30% biodiesel |

| Sample | Experiment |
|---|---|
| 5A1 | 5A + Cu |
| 5A2 | 5A + 500 ppm of 3,3-methylenebis(5-methyloxazolidine) |
| 5A3 | 5A + 500 ppm of 3,3-methylenebis(5-methyloxazolidine) + Cu |
| 5A4 | 5A + 2500 ppm of semiconcentrate X |
| 5A5 | 5A + 2500 ppm of semiconcentrate X + Cu |
| 5B1 | 5B + Cu |
| 5B2 | 5B + 500 ppm of 3,3-methylenebis(5-methyloxazolidine) |
| 5B3 | 5B + 500 ppm of 3,3-methylenebis(5-methyloxazolidine) + Cu |
| 5B4 | 5B + 2500 ppm of semiconcentrate X |
| 5B5 | 5B + 2500 ppm of semiconcentrate X + Cu |
| 5C1 | 5C + Cu |
| 5C2 | 5C + 500 ppm of 3,3-methylenebis(5-methyloxazolidine) |
| 5C3 | 5C + 500 ppm of 3,3-methylenebis(5-methyloxazolidine) + Cu |
| 5C4 | 5C + 2500 ppm of semiconcentrate X |
| 5C5 | 5C + 2500 ppm of semiconcentrate X + Cu |
| 5D1 | 5D + Cu |
| 5D2 | 5D + 500 ppm of 3,3-methylenebis(5-methyloxazolidine) |
| 5D3 | 5D + 500 ppm of 3,3-methylenebis(5-methyloxazolidine) + Cu |
| 5D4 | 5D + 2500 ppm of semiconcentrate X |
| 5D5 | 5D + 2500 ppm of semiconcentrate X + Cu |

The appearance of the individual sample changed as follows:

| | Start | After 1 week | After 2 weeks | After 3 weeks | After 4 weeks | After 5 weeks | After 6 weeks | After 11 weeks |
|---|---|---|---|---|---|---|---|---|
| 5A1 | clear red solution | clear red solution | clear red solution | clear red solution | clear red solution | clear red solution | clear red solution | clear red solution |

-continued

| | Start | After 1 week | After 2 weeks | After 3 weeks | After 4 weeks | After 5 weeks | After 6 weeks | After 11 weeks |
|---|---|---|---|---|---|---|---|---|
| 5A2 | clear red solution | clear red solution | clear red solution | clear red solution | clear red solution | clear red solution | clear red solution | clear, red, sediment on the metal and at the base |
| 5A3 | clear red solution | clear red solution | clear red solution | clear red solution | clear red solution | clear red solution | clear red solution | Slightly turbid, sediment at the base |
| 5A4 | clear red solution | clear red solution | clear red solution | clear red solution | clear red solution | clear red solution | clear red solution | clear red solution |
| 5A5 | clear red solution | clear red solution | clear red solution | clear red solution | clear red solution | clear red solution, a little fluff | clear red solution, a little fluff | clear red solution, a little fluff |
| 5B1 | clear red solution | clear red solution | clear red solution | clear red solution | clear red solution | clear red solution, a little fluff | slightly turbid, crumbs | slightly turbid, crumbs |
| 5B2 | clear red solution | clear red solution | clear red solution | clear red solution | clear red solution | clear red solution | slightly turbid, a little sediment at the base | slightly turbid, a little sediment at the base |
| 5B3 | clear red solution | turbid red liquid | dark sludge in turbid red liquid | dark sludge in turbid red liquid | dark sludge in turbid red liquid | dark sludge in turbid red liquid | dark sludge in turbid red liquid | dark sludge in turbid red liquid |
| 5B4 | clear red solution | clear red solution | clear red solution | clear red solution | clear red solution | clear red solution | slightly turbid, a little sediment at the base | slightly turbid, a little sediment at the base |
| 5B5 | clear red solution | clear red solution | clear red solution | clear red solution | clear red solution | clear red solution | slightly turbid, a little sediment at the base | slightly turbid, a little sediment at the base |
| 5C1 | clear red solution | clear red solution | clear red solution | clear red solution | clear red solution | turbid | turbid | turbid, has become lighter |
| 5C2 | clear red solution | clear red solution | clear red solution | clear red solution | clear red solution | clear red solution | slightly turbid, a little sediment at the base | slightly turbid, a little sediment a the base |
| 5C3 | clear red solution | turbid red liquid | dark sludge in turbid red liquid | dark sludge in turbid red liquid | dark sludge in turbid red liquid | dark sludge in turbid red liquid | dark sludge in turbid red liquid | dark sludge in turbid red liquid |
| 5C4 | clear red solution | clear red solution | clear red solution | clear red solution | clear red solution | clear red solution | slightly turbid, a little sediment at the base | slightly turbid, a little sediment at the base |
| 5C5 | clear red solution | clear red solution | clear red solution | clear red solution | clear red solution | clear red solution | slightly turbid, a little sediment at the base | slightly turbid, a little sediment at the base |
| 5D1 | clear red solution | clear red solution | clear red solution | clear red solution | clear red solution | turbid | turbid | decolorized to orange, turbid and sediment |
| 5D2 | clear red solution | clear red solution | clear red solution | clear red solution | clear red solution | clear red solution | slightly turbid, a little sediment at the base | slightly turbid, a little sediment a the base |

-continued

|  | Start | After 1 week | After 2 weeks | After 3 weeks | After 4 weeks | After 5 weeks | After 6 weeks | After 11 weeks |
|---|---|---|---|---|---|---|---|---|
| 5D3 | clear red solution | turbid red liquid | dark sludge in turbid red liquid | dark sludge in turbid red liquid | dark sludge in turbid red liquid | dark sludge in turbid red liquid | dark sludge in turbid red liquid | dark sludge in turbid red liquid |
| 5D4 | clear red solution | clear red solution | clear red solution | clear red solution | clear red solution | clear red solution | slightly turbid | slightly turbid |
| 5D5 | clear red solution | clear red solution | clear red solution | clear red solution | clear red solution | clear red solution | slightly turbid | slightly turbid |

Evaluation of the Examples

Example 1 shows that 3,3'-methylenebis(5-methyloxazolidine) is incompatible as an additive to diesel oil (with 5% FAME) with a time delay and in a concentration-dependent manner and more particularly in turbulent flow, when it comes into contact with copper or nonferrous metal. 3,3-Methylenebis(5-methyloxazolidine) is thus, as an additive to diesel/biodiesel, associated with disadvantages when there is contact with nonferrous metal. The biocide, which in principle has good suitability, is thus not very suitable owing to its incompatibility.

Example 2 shows that diesel fuel with 5% FAME can leach considerable amounts of copper salt out of copper sheet (2B). In the case of addition of 3,3'-methylenebis(5-methyloxazolidine), the copper wear is lower (2D), and in the case of addition of inventive semiconcentrate with ShellSol A 150 significantly lower (2F). The formation of sludge in the solution correlates with the amount of copper salt released. Even in the absence of copper sheet, the performance of the inventive semiconcentrate is somewhat better than that of 3,3'-methylenebis(5-methyloxazolidine) (see 2E compared to 2C).

Example 3 shows that diesel fuel with 5% FAME in contact with copper sheet is protected better by addition of a concentrate composed of 92% 3,3'-methylenebis(5-methyloxazolidine), 4% 2,6-di-tert-butylphenol and 4% Irgamet 30 than by addition of a likewise inventive concentrate composed of 92% 3,3'-methylenebis(5-methyloxazolidine), 4% BHT and 4% benzotriazole.

In Example 4, a defined amount of copper salt (copper naphthenate, dissolved in toluene) is added to diesel fuel with 5% FAME (4D to 4I). WHEN 3,3'-methylenebis(5-methyloxazolidine) is added, there is incompatibility depending on the copper concentration (4D, 4E). An addition of inventive semiconcentrate significantly improves the stability of the diesel fuel (4F, 4G). Diesel fuel with 5% FAME leads, after addition of copper salt, to the formation of sludge (see 4H, 4I). Diesel fuel with 5% FAME without addition of copper salt is stable (4A), and likewise in the case of addition of 3,3'-methylenebis(5-methyloxazolidine) (4B) or inventive semiconcentrate (4C). This demonstrates that inventive semiconcentrates are also suitable for products which do not have a proportion of material composed of renewable raw materials.

Example 5 shows the unfavourable influence of FAME (10 to 30% by volume) on diesel fuel when the latter is in contact with Cu. An addition of 3,3'-methylenebis(5-methyloxazolidine) worsens the compatibility further (e.g. 5C3 compared to 5C1); only an addition of inventive semiconcentrate gives a stable liquid in the presence of copper sheet (e.g. 5C5).

This shows that an N-formal such as 3,3'-methylenebis(5-methyloxazolidine) is incapable of protecting FAME-containing liquids which are in contact with nonferrous metals against microbial degradation. Only the combination with sufficient amounts of antioxidant and corrosion inhibitor leads to a product which protects FAME-containing liquids which are in contact with nonferrous metals from microbial degradation. FAME-containing liquids are then storage-stable and do not form undesired precipitates.

The invention claimed is:

1. An additive mixture for fuels as a liquid concentrate, consisting of:
   a) 92% by weight of N,N'-methylenebis (5-methyloxazolidine);
   b) 4% by weight of 2,6-di-tert-butylphenol as an antioxidant; and
   c) 4% by weight of N,N-bis(2-ethylhexyl) (1,2,4-triazol-1-ylmethyl)amine as a corrosion inhibitor.

2. A method for producing a semiconcentrate comprising dissolving the additive mixture as a liquid concentrate according to claim 1 in a carrier, said dissolved liquid concentrate in said carrier being a semiconcentrate.

3. The method according to claim 2, wherein said carrier is selected from the group consisting of diesel oil, biodiesel oil, fatty acid methyl esters, mineral oil, aliphatic or aromatic hydrocarbons and mixtures thereof, and said carrier is at least 50% by weight of said semiconcentrate.

4. A method for operating a system with fuel, in which the additive mixture as a liquid concentrate according to claim 1 is added to the fuel.

5. A semiconcentrate consisting of:
   a carrier is selected from the group consisting of diesel oil, biodiesel oil, fatty acid methyl esters, mineral oil, aliphatic or aromatic hydrocarbons and mixtures thereof; and
   the additive mixture as a liquid concentrate according to claim 1 dissolved in said carrier.

6. The semiconcentrate according to claim 5, wherein said carrier is at least 50% by weight of said semiconcentrate.

7. The semiconcentrate according to claim 5, wherein,
   said N,N'-methylenebis (5-methyloxazolidine) is 20% by weight of said concentrate,
   said 2,6-di-tert-butylphenol is 0.9% by weight of said concentrate; and
   said N,N-bis(2-ethylhexyl)(1,2,4-triazol-1-ylmethyl) amine is 0.9% by weight of said concentrate.

8. A method for biocidal and corrosion-inhibiting additization of a fuel that flows through or is stored in a system comprising copper-containing material in contact with said fuel, comprising:
   adding to said fuel a liquid concentrate consisting of:
   a) N,N'-methylenebis (5-methyloxazolidine);
   b) an antioxidant selected from the group consisting of sterically hindered phenols, amines, vitamin E and derivatives thereof, alkyl gallates and mixtures thereof; and c) a corrosion inhibitor selected from the group consisting of benzotriazole, tolyltriazole, N,N-bis(2-ethylhexyl)(1,2,4-triazol-1-ylmethyl) amine and mixtures thereof, said antioxidant and said corrosion inhibitor being present in a weight ratio of 1:10 to 10:1, and for 100% of said concentrate, said antioxidant and said corrosion inhibitor are each at least 2% by weight, wherein corrosion of copper in a system through which the fuel flows or in which the fuel is stored is inhibited.

9. The method according to claim 8, wherein the fuel comprises proportions of fatty acid methyl esters.

10. The method according to claim 9, wherein the proportion of the fatty acid methyl esters is up to 100% by volume.

11. The method according to claim 8, wherein the liquid concentrate is used in an amount of 20 to 1000 ppm.

12. A fuel comprising at least 5 ppm of N,N'-methylenebis(5-methyloxazolidine);

at least 0.25 ppm of an antioxidant comprising 2,6-di-tert-butylphenol and BHT at least 5 ppm a corrosion inhibitor selected from the group consisting of benzotriazole, tolyltriazole, N,N-bis(2-ethylhexyl) (1,2,4-triazol-1-ylmethyl)amine and mixtures thereof, and fatty acid methyl esters wherein said antioxidant and said corrosion inhibitor are present in a weight ratio of 1:10 to 10:1, wherein said fuel is selected from the group consisting of biofuels, biodiesels, diesel fuels, kerosenes, heavy oils, heating oils, and mineral oils.

13. The fuel according to claim 12, wherein said N,N'-methylenebis(5-methyloxazolidine), said antioxidant, and said corrosion inhibitor are present together in said fuel in an amount of 20 to 1000 ppm.

* * * * *